United States Patent
Hyman et al.

(10) Patent No.: US 10,774,300 B2
(45) Date of Patent: Sep. 15, 2020

(54) METHODS AND KITS FOR ISOLATING MICROORGANISMS FROM CULTURE

(75) Inventors: Jones M. Hyman, Wake Forest, NC (US); John D. Walsh, Durham, NC (US); Ronnie J. Robinson, St. Charles, MO (US); Christopher Ronsick, Durham, NC (US)

(73) Assignee: bioMerieux, Inc., Durham, NC (US)

( * ) Notice: Subject to any disclaimer, the term of this patent is extended or adjusted under 35 U.S.C. 154(b) by 669 days.

(21) Appl. No.: 13/554,704

(22) Filed: Jul. 20, 2012

(65) Prior Publication Data
US 2013/0045532 A1    Feb. 21, 2013

Related U.S. Application Data

(60) Provisional application No. 61/510,862, filed on Jul. 22, 2011.

(51) Int. Cl.
*C12Q 1/689* (2018.01)
*C12Q 1/6888* (2018.01)
(Continued)

(52) U.S. Cl.
CPC ............... *C12M 47/02* (2013.01); *C12N 1/02* (2013.01); *C12N 1/06* (2013.01); *C12Q 1/04* (2013.01);
(Continued)

(58) Field of Classification Search
CPC .. B01D 15/363; B01D 15/3804; B01D 29/00; C12Q 1/6806; C12Q 2527/125;
(Continued)

(56) References Cited

U.S. PATENT DOCUMENTS

| 5,556,598 A | 9/1996 | Raybuck et al. |
| 5,833,927 A | 11/1998 | Raybuck et al. |

(Continued)

FOREIGN PATENT DOCUMENTS

| EP | 0465987 A2 | 1/1992 |
| EP | 1829958 A1 | 9/2007 |

(Continued)

OTHER PUBLICATIONS

O'Mahony, K. et al., "Proposal for a better integration of bacterial analysis . . . " J. of Biotechnology, Elsevier Science Publishers, Amsterdam, NL, vol. 119, No. 2, Jul. 1, 2005, pp. 118-132.

(Continued)

*Primary Examiner* — Neil N Turk (57) ABSTRACT

The present invention is directed to methods and kits for separating, accumulating, characterizing and/or identifying microorganisms known to be present or that may be present in a test sample. The method of the invention comprises optional lysing non-microorganism cells and/or particulates that may be present in a test sample, followed by a subsequent filtration step for isolation and/or accumulation of microorganisms. The kit of the present invention may comprise at least one filter membrane or an integrated filtration and sample transfer device for isolation and/or accumulation of microorganisms.

6 Claims, 5 Drawing Sheets

Step 1 Positive BC Sample
Step 2 Add Lysis Buffer
Step 3 Isolate and Accumulate Microbes by Vacuum Filtration
Step 4 Wash Microbes on Filter
Step 5 Harvest Microbes (51) Int. Cl.
*C12M 1/00* (2006.01)
*C12Q 1/04* (2006.01)
*C12N 1/02* (2006.01)
*C12N 1/06* (2006.01)
*C12Q 1/6895* (2018.01)
*C12Q 1/24* (2006.01)

(52) U.S. Cl.
CPC ............... *C12Q 1/045* (2013.01); *C12Q 1/24* (2013.01); *C12Q 1/689* (2013.01); *C12Q 1/6888* (2013.01); *C12Q 1/6895* (2013.01)

(58) Field of Classification Search
CPC ........... C12Q 2527/137; C12N 15/101; C12N 15/87; C12N 15/1006; C12N 15/1017; G01N 30/461; Y10S 435/81; Y10S 435/82; Y10S 436/808
USPC .......................................................... 435/6.1
See application file for complete search history.

(56) References Cited

U.S. PATENT DOCUMENTS

| | | | |
|---|---|---|---|
| 6,221,655 B1* | 4/2001 | Fung | B01L 3/5021 422/504 |
| 6,746,513 B2 | 6/2004 | Anderson | |
| 7,790,865 B1* | 9/2010 | Heath et al. | 536/23.1 |
| 2003/0129600 A1* | 7/2003 | Morrison | C12Q 1/6895 435/6.13 |
| 2003/0175166 A1 | 9/2003 | Schluter | |
| 2006/0081524 A1* | 4/2006 | Sengupta | B01D 19/0031 210/321.88 |
| 2007/0003997 A1 | 1/2007 | Kemmochi | |
| 2007/0207518 A1* | 9/2007 | Motoyama | C12Q 1/04 435/34 |
| 2008/0044841 A1 | 2/2008 | Viedma | |
| 2009/0280471 A1* | 11/2009 | Ecker | C12Q 1/701 435/5 |
| 2010/0120085 A1* | 5/2010 | Hyman | C12Q 1/04 435/34 |
| 2010/0240023 A1 | 9/2010 | Hermet | |
| 2011/0159533 A1* | 6/2011 | Karkouche | B01L 3/502 435/29 |

FOREIGN PATENT DOCUMENTS

| | | |
|---|---|---|
| WO | 0149872 A2 | 7/2001 |
| WO | 2003016552 A2 | 2/2003 |
| WO | 0188501 A1 | 9/2003 |
| WO | 2005093045 A2 | 10/2005 |
| WO | 2009018544 A1 | 2/2009 |
| WO | 2012083150 A2 | 6/2012 |

OTHER PUBLICATIONS

Ulrich, R. et al., "Reproducible Filtration of Bacteria with Micromechanical Filters" J. of Rapid Methods in Automation in Microbiology, vol. 16, No. 4, Dec. 1, 2008, pp. 337-350.
Extended European Search Report, dated Mar. 17, 2015.
Ribault, S. et al., "Detection of Bacteria in Red Blood Cell Concentrates by the Scansystem Method" J. of Clinical Microbiology, American Society for Microbiology, vol. 43, No. 5, May 2005, pp. 2251-2255.

* cited by examiner

METHODS AND KITS FOR ISOLATING MICROORGANISMS FROM CULTURE

CROSS REFERENCE TO RELATED APPLICATION

This application claims the benefit of U.S. Provisional Patent Application No. 61/510,862, entitled, "Method and Kit for Isolating Microorganisms from Culture", filed Jul. 22, 2011, which is incorporated herein.

FIELD OF THE INVENTION

The present invention is directed to methods and kits for isolating, accumulating and/or purifying microorganisms from a sample. More specifically, the present invention relates to a method and kit for the isolation, accumulation and/or purification of microorganisms from a liquid sample (e.g., culture media or a blood culture) by filtration.

BACKGROUND OF THE INVENTION

The detection of pathogenic microorganisms in biological fluids should be performed in the shortest possible time, in particular in the case of septicemia for which the mortality remains high in spite of the broad range of antibiotics which are available to doctors. The presence of biologically active agents such as a microorganism in a patient's body fluid, especially blood, is generally determined using blood culture bottles. Bloodstream infections are associated with high morbidity and mortality, yet current diagnostic methods, of culture followed by biochemical identification and antibiotic susceptibility testing, can take several days to perform. Typically, empiric therapy is initiated based on clinical symptoms, and test results only impact clinical decisions when the initial therapy fails. The ability to characterize bloodstream infections within the first few hours, preferably within an hour after a positive blood culture result would significantly boost the clinical relevance of the diagnostic information provided. Molecular amplification methods have been proposed to fill this need, but serious challenges to this approach remain. The positive blood culture broth itself represents a naturally amplified population of microorganisms with potential for use in a variety of rapid, identification (ID) tests.

Traditional automated phenotypic ID tests, such as the VITEK®, PHOENIX®, and MICROSCAN® systems, or manual phenotypic tests such as API require that microorganisms be in an appropriate growth phase and free of interfering media and blood products in order to provide robust results. These systems use colonies grown from the positive broth for 18-24 hours on plated media. However, in an effort to obtain faster results, some laboratories have reported using these systems with microorganisms isolated from positive blood culture bottles. These direct-from-the-bottle tests are not appropriate for all microorganisms (e.g., Gram-positive cocci), are not validated by the test manufacturers, and generally take 3-8 hours to provide results. Faster and more broadly specific tests are urgently needed in order to provide the physician with clinically relevant results within the first few hours, preferably within an hour after a positive culture result.

Mass spectrometric methods have the potential to allow for identification of microorganisms very quickly, but may encounter interference from the many compounds present in liquid microbiological culture media and in clinical samples such as blood or combinations thereof. The most commonly employed methods for recovering microorganisms directly from positive blood culture broth are two-step differential centrifugation and centrifugation in a serum separator tube.

Other methods for separation, characterization and/or identification of microorganisms have been described, include:

In U.S. Pat. No. 7,070,739 a method is presented to extract, separate, and purify microbes including viruses by two-dimensional ultra-centrifuging directly from body fluids or homogenized tissue. In a first centrifuging step, all particles are removed having a sedimentation speed higher than those of the microbes to be identified. In the second ultra-centrifuging step, isopycnic banding is used in liquids filled in to form a wide-range density gradient, using special serrated centrifuge tubes. According to the patent, the separation technique can be used for detecting banded particles by light scatter or fluorescence using nucleic acid specific dyes, and for recovering the banded particles in very small volumes for characterization by mass spectrometry of viral protein subunits and intact viral particles, and by fluorescence flow cytometric determination of both nucleic acid mass and the masses of fragments produced by restriction enzymes.

EP0533912A describes a sample pretreatment apparatus and method for dialysis fluid and urine. The patent application describes the use of a large pore size pre-filter to remove typical urinary sediments such as blood cells, epithelial cells, casts, mucus and crystals. Any bacteria present pass through the pre-filter and are captured on a second downstream filter. Captured bacteria are then accessed by manually disassembling the stacked apparatus.

U.S. Pat. Appl. Pub. No. 2007/0175278 describes using a liquid culture medium for culturing a sample of interest, including for example, blood, urine, feces, intravenous catheters etc., industrial production lines, water systems, a food product, a cosmetic product, a pharmaceutical product and a forensic sample. Subsequently, the microorganisms can be harvested from the liquid medium by methods known in the art, e.g. by centrifugation. The concentrated microorganisms may then be transferred to carrier material, optionally after drying, for obtaining a vibrational spectrum. The patent application discusses various methods for identifying and classifying microorganisms, including vibrational spectroscopy, such as Raman spectroscopy.

However, these methods have several drawbacks when attempting to separate and characterize microorganisms from some clinical test samples (e.g., complex samples such as blood-containing culture media). In the case of blood-containing culture media, the resultant microbial preparations often contain contaminating red blood cells, platelets, lipid particles, plasma enzymes and cellular debris, which can cause poor results. These methods are also very labor-intensive and unsafe due to steps which can result in aerosol exposure of potentially dangerous pathogens to the user.

Co-assigned U.S. Pat. Appl. Pub. No. 2010/0120085, which is incorporated herein, describes methods for separating, characterizing and/or identifying microorganisms in a test sample. The method described a sample preparation procedure comprising of a selective lysis step and subsequent separation step for the isolation and purification of an unknown microorganism from a test sample for identification of the microorganism using mass spectrometry. The application also describes using filtration for the isolation and purification of an unknown microorganism from a test sample.

Nevertheless, there remains a need for improved sample preparation methods and kits for the isolation, accumulation and/or purification of microorganisms from clinical test samples, which are compatible with rapid identification technologies such as mass spectrometry. The methods and devices described herein produce a clean, concentrated, sample of microorganisms that is optimal for analysis, for example, by mass spectrometry, especially for MALDI-TOF MS analysis.

SUMMARY OF THE INVENTION

The present invention is directed to methods and kits for isolating, accumulating and/or purifying microorganisms from a test sample (e.g., a culture medium). The isolated, accumulated and/or purified microorganisms can then be used for a variety of direct test applications (e.g., spectroscopy, mass spectrometry, molecular, immuno, latex tests, etc)

In one aspect, the present invention is directed to a method of isolating, accumulating and/or purifying a microorganism from a test sample, comprising:
(a) obtaining a test sample known to contain or that may contain microorganisms;
(b) optionally lysing non-microorganism cells and/or particulates in said test sample producing a lysed sample; and
(c) isolating and accumulating said microorganisms from other components of said test sample or said lysed sample by filtration using a filtration membrane and/or filtration device.

In one embodiment, the isolated or accumulated sample of microorganisms can be analyzed or interrogated for characterization and/or identification of the microorganism. Typically, any known means in the art for characterization and/or identification of an unknown microorganism can be used. For example, the isolated and/or accumulated sample of microorganism can be analyzed or interrogated using spectroscopic interrogation, e.g., based on intrinsic characteristics of the microorganisms (e.g., intrinsic fluorescence) or the vibrational structure of constituent molecules (e.g., Raman spectroscopy). In another embodiment, the isolated or accumulated microorganisms can be analyzed by mass spectrometry (e.g., MALDI-TOF-MS).

In another aspect, the present invention is directed to a method of isolating, accumulating and/or purifying a microorganism from a blood culture, comprising:
(a) obtaining a sample from a blood culture known to contain or that may contain microorganisms;
(b) optionally lysing non-microorganism cells and/or particulates in said sample to produce a lysed sample;
(c) isolating and accumulating said microorganisms from other components of said lysed sample by filtration using a filtration membrane and/or filtration device.

In yet another aspect, the present invention is directed to a kit for the isolation, accumulation and/or purification of microorganisms from a test sample comprising, in packaged combination:
(a) optionally a selective lysis solution or buffer for the selective lysis of non-microorganisms known to be present or that may be present in a test sample;
(b) at least one filter membrane having a pore size which is small enough to prevent passage of microorganisms through the filter but allows other components in the sample, (e.g., lysed non-microorganism cells and/or debris) to pass through the filter; and
(c) at least one wash buffer for washing the isolated, accumulated and/or purified microorganism sample.

In one embodiment, the kit may further comprise a container (e.g., a tube), within which the lysis step can be carried out. In yet another embodiment, the filtration device may be a side-arm vacuum flask with reusable filter holder or a manifold with a filtrate reservoir optionally having a plurality of reusable ports or filter holders. In still other embodiments, the kit may further comprise additional components for filtration, for example, the kit may comprise one or more tubes, clamps, valves or vacuum traps. In another embodiment, the kit may comprise one or more disposable filter units having a built in filtration membrane. In these disposable filter units, filtration may be enabled by either a vacuum source of by centrifugation. In still another embodiment, the kit may further comprise a vacuum source, vacuum system or a centrifuge.

In another aspect, the present invention is directed to a kit for the isolation, accumulation and/or purification of microorganisms from a test sample comprising, in a packaged combination:
(a) optionally a selective lysis solution or buffer for the selective lysis of non-microorganism known to be present or that may be present in a test sample;
(b) at least one integrated filtration and sample transfer device for the isolation, accumulation and/or purification of microorganisms from a test sample, and for the subsequent harvesting and transfer of microorganisms; and
(c) at least one wash buffer for washing the isolated, accumulated and/or purified microorganism sample.

DETAILED DESCRIPTION OF THE INVENTION

Definitions.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "microorganism" is intended to encompass organisms that are generally unicellular, which can be multiplied and handled in the laboratory, including but not limited to, Gram-positive or Gram-negative bacteria, yeasts, molds, parasites, and mollicutes. Non-limiting examples of Gram-negative bacteria of this invention include bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia*, and *Legionella*. Non-limiting examples of Gram-positive bacteria of this invention include bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus, Mycobacteria* and *Corynebacteria*. Non-limiting examples of yeasts and molds of this invention include those of the following genera: *Candida, Cryptococcus, Nocardia, Penicillium, Alternaria, Rhodotorula, Aspergillus, Fusarium, Saccharomyces* and *Trichosporon*. Non-limiting examples of parasites of this invention include those of the following genera: *Trypanosoma, Babesia, Leishmania, Plasmodium, Wucheria, Brugia, Onchocerca*, and *Naegleria*. Non-limiting examples of mollicutes of this invention include those of the following genera: *Mycoplasma* and *Ureaplasma*.

In one embodiment, as described in further detail herein, microorganisms from a sample or growth medium can be "separated" or "isolated." As used herein, the term "separate" is intended to encompass any sample of microorganisms that has been removed, concentrated or otherwise set apart from its original state, or from a growth or culture medium. For example, in accordance with this invention, microorganisms may be separated away (e.g., as a separated sample or mass of microorganism) from non-microorganism or non-microorganism components that may otherwise interfere with any subsequent characterization and/or identification of the unknown microorganism by known means in the art (e.g., by mass spectrometry). The term may include a layer of microorganisms collected on a solid surface (e.g., a filter membrane). As such, a separated microorganism sample (or mass or thin film of microorganism) may include any collection or layer of microorganisms and/or components thereof that is more concentrated than, or otherwise set apart from, the original sample, and can range from a closely packed dense clump of microorganisms to a diffuse layer of microorganisms. Microorganism components that can be comprised in a separated form or sample include, without limitation, pilli, flagella, fimbriae, and capsules in any combination. Non-microorganism components that are separated away from the microorganisms may include non-microorganism cells (e.g., blood cells and/or other tissue cells), urine casts or crystals and/or any components thereof. As used herein, the term "isolated" is intended to encompass any sample of microorganisms that has been at least partially purified from its original state, or away from a growth or culture medium, and any non-microorganisms or non-microorganism components contained therein. For example, in accordance with this invention, microorganisms may be isolated away (e.g., as an isolated sample) from non-microorganisms or non-microorganism components that may otherwise interfere with any subsequent characterization and/or identification of the unknown microorganism by means known in the art (e.g., by mass spectrometry). Non-microorganism components that are separated away from the microorganisms may include non-microorganism cells (e.g., blood cells and/or other tissue cells) and/or any components thereof.

In one embodiment, as described in further detail herein, microorganisms from a sample or growth medium can be "accumulated" or "captured" in, or on a filter material (e.g., a filter membrane). As used herein, the term "accumulated" or "captured" is intended to encompass any sample of microorganisms that has been compressed or deposited into a mass or film of microorganisms. For example, microorganisms from a sample can be compressed or deposited into a mass or film on a filtration material (e.g., a filter membrane) by filtration. The term includes a collection of microorganisms (and/or components thereof) on the surface of a filter material (e.g., a filter membrane) following filtration (e.g., vacuum filtration). Microorganism components that can be comprised in compressed or deposited mass of microorganisms include, without limitation, pilli, flagella, fimbriae, and capsules in any combination. In accordance with this invention, microorganisms may be compressed or deposited into a mass away (e.g., as a substantially purified microorganism mass) from non-microorganism or non-microorganism components that may otherwise interfere with any subsequent characterization and/or identification of the microorganism, for example, by mass spectrometry. Non-microorganism components that are isolated or separated away from the microorganisms may include non-microorganism cells (e.g., blood cells and/or other tissue cells) and/or any components thereof.

As used herein, the term "analyzing said isolated or accumulated sample" is intended to encompass all well known methods or means for analyzing, interrogating, obtaining or otherwise acquiring measurements or data that can be used for the characterization and/or identification of microorganisms (e.g. unknown microorganisms). For example, an isolated or accumulated mass of microorganisms can be analyzed or interrogated by spectroscopic methods, e.g., based on intrinsic characteristics of the microorganisms (e.g., intrinsic fluorescence) or the vibrational structure of constituent molecules (e.g., Raman spectroscopy). In another embodiment, an isolated or accumulated mass of microorganisms can be analyzed or interrogated by mass spectrometry methods (e.g., MALDI-TOF-MS) for the acquisition or measurements or data that can be used for the characterization and/or identification of unknown microorganisms, as discussed in further detail hereinbelow.

Detailed Description.

In its simplest form, the method of the present invention involves a three step process: (1) obtaining a test sample known to contain or that may contain microorganisms; (2) an optional lysis step for the selective lysis of non-microorganism cells and/or particulates in said sample to produce a lysed sample; and (3) a filtration step to isolate, accumulate and/or purify any microorganism that may be in test sample. Optionally, the isolated, accumulated and/or purified microorganisms can be harvested or collected after the filtration step, for example, using a micro-swab.

The steps involved in the methods of the invention, from obtaining a sample to isolation, accumulation and/or purification of microorganisms, can be carried out in a very short time frame to obtain clinically relevant actionable information. In certain embodiments, the methods of the invention can be carried out in less than about 60 minutes, e.g., in less than about 50, 40, 30, 20, 10, 5 minutes.

The methods can be used to isolate, accumulate and/or purify any microorganism as described herein. In one embodiment, the microorganism is a bacterium. In another embodiment, the microorganism is a yeast. In still another embodiment, the microorganism is a mold. In a further embodiment, the microorganism is a parasite. In another embodiment, the microorganism is a mollicute. Additionally, the methods of the invention can be fully automated, thereby reducing the risk of handling infectious materials and/or contaminating the samples.

In one embodiment, the sample and the lysis solution or buffer are mixed and then incubated for a sufficient time for lysis and solubilization of cell membranes to occur, e.g., about 1, 2, 3, 4, 5, 10, 15, 20, 25, 30, 40, 50, or 60 seconds, or about 2, 3, 4, 5, 6, 7, 8, 9, 10, 15, or 20 minutes or longer, e.g., about 1 second to about 20 minutes, about 1 second to about 5 minutes, or about 1 second to about 2 minutes. In another embodiment, the sample and lysis solution are incubated from about 30 seconds to about 5 minutes, or from about 1 minute to about 3 minutes. The incubation time will depend on the strength of the lysis solution, e.g., the concentration of the detergent and/or enzymes. In general, milder lysis solutions will require more time and a greater dilution of the sample to fully solubilize non-microbial cells. The strength of the lysis solution can be selected based on the microorganisms known to be or suspected to be in the sample. For microorganisms that are more susceptible to lysis, a mild lysis solution can be used. The lysis can take place at a temperature of from about 0° C. to about 60° C., from about 15° C. to about 40° C., from about 20° C. to about 40° C., or from about 30° C. to about 40° C.

The next step in the method of the present invention (e.g., the step after the sample has been lysed, if a lysing or dissolving step is performed) is a separation, isolation and/or accumulation step. The separation, isolation and/or accumulation step can be carried out to separate and isolate or purify the microorganisms from other components of the sample (e.g., non-microorganisms or components thereof) and to accumulate or capture the microorganisms into a mass that can be used for subsequent testing, for example, for characterization and/or identification. The separation, isolation and/or accumulation does not have to be complete, i.e., it is not required that 100% separation occur. All that is required is that the separation, isolation and/or accumulation of the microorganisms from other components of the sample be sufficient to permit analysis or interrogation of the microorganisms without substantial interference from the other components. For example, the separation/isolation can result in an accumulated or captured microorganism mass that is at least about 10, 20, 30, 40, 50, 60, 70, 80, 90, 95, 96, 97, 98, or 99% pure or higher.

Figure 2:
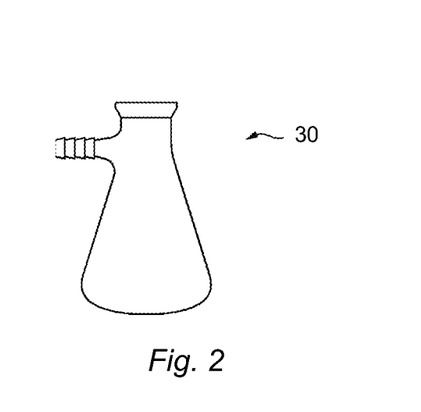
FIG. 2 shows a photograph of an example filtration device (a side-arm vacuum flask) that may be used in the methods or kits of the present invention.
Figure 3:
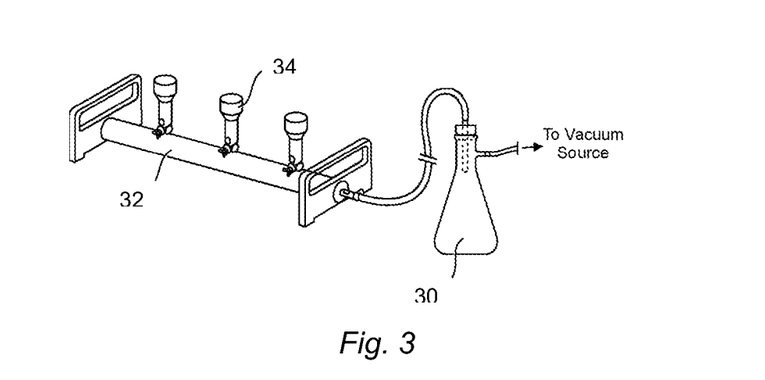
FIG. 3 shows a schematic of another possible embodiment of a filtration device comprising a filter manifold having a plurality of reusable ports or filter holders that may be used in the methods or kits of the present invention.
Figure 4A:
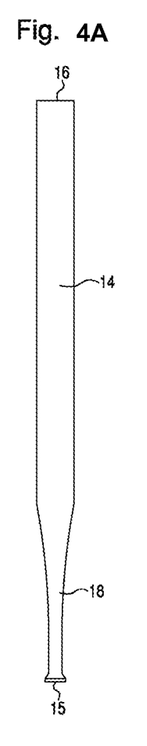
FIG. 4A shows a front view of second design concept of an integrated filtration and sample transfer device, in accordance with the present invention.

The filtration step is performed by passing the liquid sample through a filter having a pore size which retains microorganisms on the filter but allows other components in the sample, (e.g., lysed non-microorganism cells and/or debris) to pass through the filter. Suitable filters for this purpose are depth filters made up of randomly stratified fibers, and having a pore size from about 0.05 to about 1.0 m, or a pore size from about 0.1 to about 0.8 m. Such matrix materials include, but are not intended to be limited to, cotton, glass fiber, woven materials as cloth, nylon, or other polymeric material. The method of the invention can be practiced using any filtration device or system, including laboratory devices in which vacuum is used to draw liquid through the filter. An example filtration device and system are shown in FIGS. 2-4.

In accordance with the present invention, the separation, isolation and/or accumulation step is carried out as a filtration step, which allow the microorganisms to be separated, isolated and/or accumulated (e.g., the microorganisms can be accumulated or captured on the filtration material (e.g., a filter membrane) away from other components that may be present in the sample. In accordance with this embodiment, other components of the sample (e.g., non-microorganisms or components thereof that may be present in the sample medium) pass through the filter material. Accordingly, this filtration step isolates, separates and/or accumulates the microorganisms away from materials in the sample, such as medium, cell debris, and/or other components that might interfere with any subsequent testing, for example, analysis or interrogation of the microorganisms for characterization and/or identification (e.g., by mass spectrometry).

Figure 1:
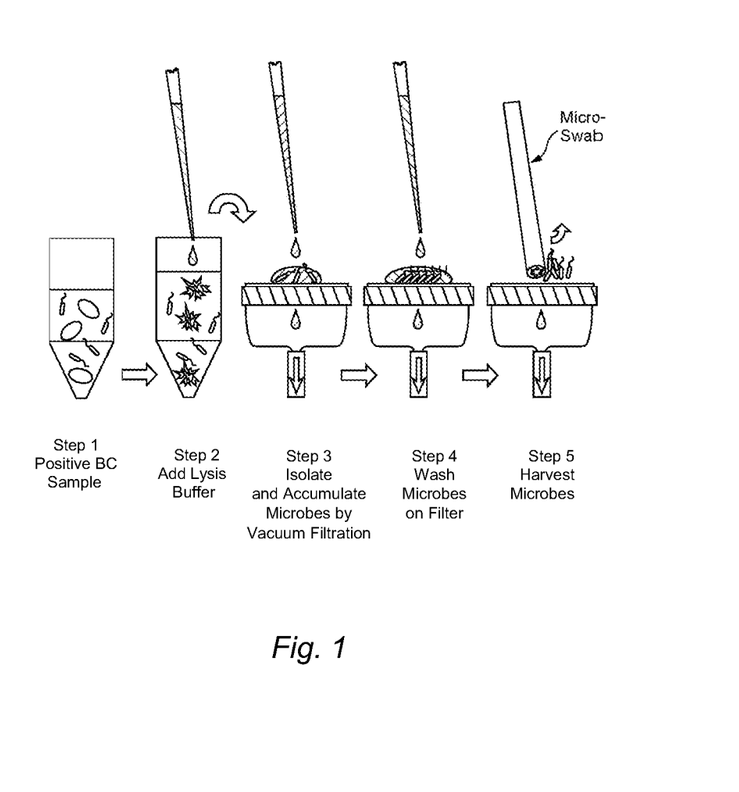
FIG. 1 shows a schematic representation of a method in accordance with the present invention. The method comprising the steps of: (1) obtaining a test sample; (2) selectively lysing non-microorganisms that may be present in the sample; (3) isolating, accumulating and/or purifying microorganisms; (4) washing the isolated microorganisms with a wash buffer; and (5) optionally harvesting or collecting the isolated microorganisms (e.g., using a micro-swab).

Accordingly, this disclosure describes a method to rapidly process microorganisms from a sample (e.g., a positive liquid culture), facilitated by a filtration step, for isolation, accumulation and/or purification of the microorganism. Referring to now to FIG. 1, an exemplified method for the separation/isolation, capture and accumulation, and optional harvesting of is shown. As shown in FIG. 1, the method involves the following steps: (1) obtaining a test sample known to contain, or that may contain a microorganism (e.g., a positive blood culture) (labeled as step 1); (2) adding a selective lysis solution or buffer to the test sample to selectively lyse any non-microorganism cells present in the test sample, thereby producing a lysed sample (step 2); (3) transferring the lysed sample to a filtration device having a filter material and applying a vacuum to the filtration device, thereby filtering the lysed sample through the filter material (e.g., filter membrane), thereby isolating, accumulating and/or purifying the microorganism on the filter material (step 3); (4) washing the isolated, accumulated and/or purified microorganism using a wash buffer (step 4); and (5) optionally harvesting the isolated, accumulated and/or purified microorganisms, for example, using a micro-swab.

In one embodiment, a method for the isolation, accumulation and/or purification of a microorganism from a blood culture comprises the following sequential steps:
(1) transfer of a blood culture sample (e.g., a 2 ml sample from a positive blood culture bottle) to a container or tube;
(2) adding a selective lysis solution or buffer (e.g., 1 ml of lysis solution) to the container or tube;
(3) mixing the blood culture sample and lysis solution (e.g., by vortex the tube);
(4) incubate the sample (e.g., for 2 min at room temperature) to form a lysed sample;
(5) applying the lysed sample to filter membrane, while pulling a vacuum through the filter material from a vacuum source to isolate, accumulate or purify microorganisms on the filter membrane;
(6) apply at least one wash buffer to the filter membrane; and allow to fully pass through the membrane; and
(10) optionally harvesting the isolated, accumulated or purified microorganism from the filter material (e.g., with a transfer device).

In another embodiment, an integrated filtration and sample transfer device, for example, as disclosed in co-pending U.S. provisional patent application, Ser. No. 61/424,418, entitled "Methods for the Isolation, Accumulation, Characterization and/or Identification of Microorganisms using a Filtration and Sample Transfer Device" (which is incorporated herein), may be used in the method of the present invention. Briefly, the filtration and sample transfer device is operable for separation, capture and accumulation of microorganisms from a test sample by vacuum filtration, and subsequent transfer of the captured and accumulated microorganisms (e.g., as a mass or film) to a test slide or plate for analysis or interrogation of the microorganisms (e.g., by mass spectrometry). In one embodiment, the filtration and sample transfer device comprises an integrated filtration and sample transfer device having a hollow elongated body (e.g., a cylindrical, hexagonal, or similarly shaped elongated hollow tube) having a first end that is provided with, or capped with a filtration material (e.g., a filtration membrane) and a second end adapted for connection to a vacuum system or device. The hollow cylindrical shaped body can be made of glass, plastic, metal or other material.

Figure 6:
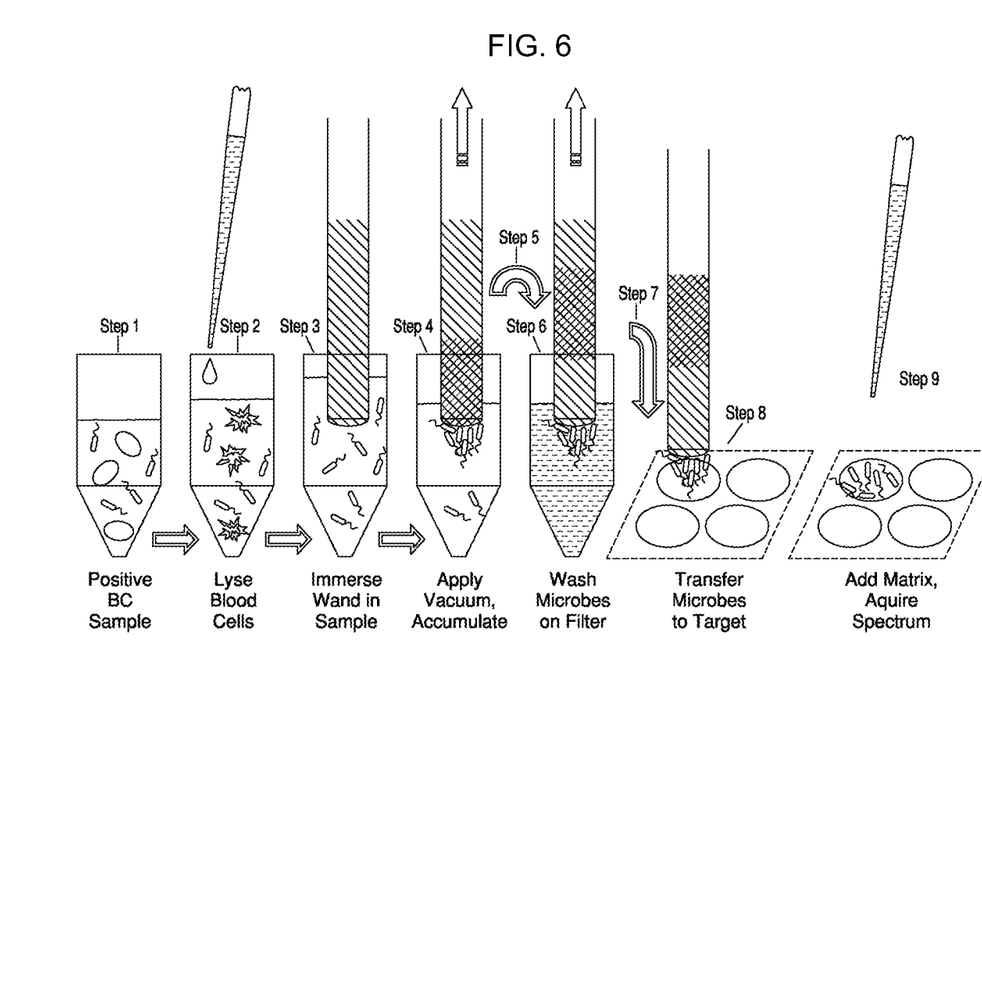
FIG. 6 shows a schematic representation of a method comprising a lysis step, separation step and transfer step, facilitated with the integrated filtration and sample transfer device of FIGS. 4-5.

In accordance with this embodiment, the method involves capture and accumulation of microorganisms on, or in a filter material, and subsequent transfer of the accumulated microbes to a slide or target plate for mass spectrometric analysis. Referring to now to FIG. 6, an exemplified method for the separation/isolation, capture and accumulation, and subsequent transfer of microorganisms for mass spectrometric analysis is shown. As shown in FIG. 6, the method involves the following steps: (1) obtaining a test sample known to contain, or that may contain a microorganism (e.g., a positive blood culture) (labeled as step 1); (2) selectively lysing the non-microorganism cells in the test sample, thereby producing a lysed sample (step 2); (3) immersing a filtration and sample transfer device (as described elsewhere herein) into the lysed sample (step 3); (4) applying a vacuum to the filtration and sample transfer device, thereby filtering the lysed sample up through the filter, thereby capturing the microorganism on the filter material of the integrated filtration and transfer device (step 4); (5) transferring the filtration and transfer device to a wash fluid or buffer, for washing the filter (step 5); (6) washing the filter by applying, or pulling a vacuum in the filtration and transfer device, thereby pulling the wash fluid or buffer up through the filter, and thus, washing any microorganisms captured on the filter material (step 6); (7) transferring the filtration and transfer device to a MALDI-TOF target plate (described in more detail below) (step 7); (8) depositing the microorganisms on the surface of the MALDI-TOF target plate (e.g., using a dabbing technique) (step 8); (9) adding matrix solution to the microorganism sample on the plate (described in more detail below) (step 9); and (10) acquiring a mass spectra of the microorganism sample using MALDI-TOF (as described below) (not shown).
Test Samples.

Test samples from which microorganism may be isolated, accumulated and/or purified by the methods and kit of the present invention include both clinical and non-clinical samples in which microorganism presence and/or growth is or may be suspected, as well as samples of materials that are routinely or occasionally tested for the presence of microorganisms. The amount of sample utilized may vary greatly due to the versatility and/or sensitivity of the method. Sample preparation can be carried out by any number of techniques known to those skilled in the art although one of the advantages of the present invention is that complex sample types, such as, e.g., blood, bodily fluids, and/or other opaque substances, may be tested directly utilizing the system with little or no extensive pretreatment. In one embodiment, the sample is taken from a culture. In another embodiment, the sample is taken from a microbiological culture (e.g., a blood culture). In another embodiment, the sample is suspected of, or known to, contain microorganisms therein.

Clinical samples that may be tested include any type of sample typically tested in clinical or research laboratories, including, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like. In another embodiment, the clinical sample can be cultured, and a culture sample used.

The present invention finds use in research as well as veterinary and medical applications. Suitable subjects from which clinical samples can be obtained are generally mammalian subjects, but can be any animal. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects. Subjects from which samples can be obtained include, without limitation, mammals, birds, reptiles, amphibians, and fish.

Non-clinical samples that may be tested also include substances, encompassing, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. The method is also particularly well suited for real-time testing to monitor contamination levels, process control, quality control, and the like in industrial settings. In another embodiment, the non-clinical sample can be cultured, and a culture sample used.

In one embodiment of the invention, samples are obtained from a subject (e.g., a patient) having or suspected of having a microbial infection. In one embodiment, the subject has or is suspected of having septicemia, e.g., bacteremia or fungemia. The sample may be a blood sample directly from the subject. The sample may be from a blood culture grown from a sample of the patient's blood, e.g., a BacT/ALERT® blood culture. The blood culture sample may be from a positive blood culture, e.g., a blood culture that indicates the presence of a microorganism. In certain embodiments, the sample is taken from a positive blood culture within a short time after it turns positive, e.g., within about 6 hours, e.g., within about 5, 4, 3, or 2 hours, or within about 60 minutes, e.g., about 55, 50, 45, 40, 35, 30, 25, 20, 15, 10, 5 minutes. In one embodiment, the sample is taken from a culture in which the microorganisms are in log phase growth. In another embodiment, the sample is taken from a culture in which the microorganisms are in a stationary phase.

In some embodiment, to aid the recovery of adherent microorganisms, e.g., from adsorbent particles, well-known pretreatment steps for adsorbent-containing samples can be used. For example, a surfactant (e.g., Tween 80) can be added and the sample and vortexed. In other embodiments, the sample can also be sonicated to break up biofilms and release intact microorganisms. Examples include *S. aureus* bound to charcoal particles.

In one embodiment of the present invention, the volume of the sample should be sufficiently large to produce an isolated and/or accumulated sample of microorganisms or a mass of microorganisms which may be subsequently analyzed or interrogated for the characterization and/or identification (e.g., by mass spectrometry) of said microorganism after the separation/isolation step of the methods of the invention is carried out. Appropriate volumes will depend on the source of the sample and the anticipated level of microorganisms in the sample. For example, a positive blood culture will contain a higher level of microorganisms per volume than a drinking water sample to be tested for contamination, so a smaller volume of blood culture medium may be needed as compared to the drinking water sample. In general, the sample size can be less than about 50 ml, e.g., less than about 40, 30, 20, 15, 10, 5, 4, 3, or 2 ml. In certain embodiments, the sample size can be about 1 ml, e.g., about 0.75, 0.5, or 0.25 ml. In certain embodiments in which the separation is carried out on a microscale, the sample size can be less than about 200 al, e.g., less than about 150, 100, 50, 25, 20, 15, 10, or 5 µl. In some embodiments (e.g., when the sample is expected to comprise a small number of microorganisms), the sample size can be about 100 ml or more, e.g., about 250, 500, 750, or 1000 ml or more.

Kit.

The present invention is also directed to a kit for the isolation, accumulation and/or purification of microorganisms from a test sample. In its simplest form, the kit of the present invention will include: (1) optionally a lysis solution or buffer for the selective lysis of non-microorganism known to be present or that may be present in a test sample; (2) a filtration membrane and/or device to isolate, accumulate and/or purify any microorganism that may be in test sample; and (3) at least one wash buffers.

In another embodiment, the present invention is also directed to a kit for the isolation, accumulation and/or purification of microorganisms from a test sample, wherein the kit comprises at least one integrated filtration and sample transfer device, as disclosed elsewhere herein. A kit in accordance with this embodiment will comprise: (1) optionally a lysis solution or buffer for the selective lysis of non-microorganism known to be present or that may be present in a test sample; (2) at least one integrated filtration and sample transfer device for isolating, accumulating and/or purifying any microorganism that may be in test sample; and (3) at least one wash buffer.

Optionally, the kit may include a selective lysis solution or buffer to selectively lyse or dissolve undesired cells and/or particulates that may be present in the test sample, e.g., blood cells and/or tissue cells. Cells and/or particulates may be lysed or dissolved to permit separation and/or isolation of microorganisms from other components of the sample. The separation and/or isolation of microorganisms from other components prevents interference during any subsequent direct testing applications, for example, analysis or interrogation for the characterization and/or identification of the microorganism (e.g., by mass spectrometry) or the performance of broad-range microbial PCR on blood culture broth. However, if non-microorganism cells are not expected to be present in the sample or not expected to interfere with any subsequent testing, the lysis step may not need to be carried out.

Typically, the selective lysis solution can be used to lyse or dissolve non-microorganism cells that may be present in the test sample. However, in some embodiments, the selective lysing of specific classes of microorganisms may be desirable and thus can be carried out according to the methods described herein and as are well known in the art. For example, a class of undesired microorganisms can be selectively lysed, e.g., yeast are lysed while bacteria are not or vice versa. In another embodiment, the desired microorganisms are lysed in order to separate a particular subcellular component of the microorganisms, e.g., cell membranes or organelles. In one embodiment, all of the non-microbial cells are lysed. In other embodiments, a portion of the non-microbial cells are lysed, e.g., enough cells to prevent interference with the interrogation step. The lysing of cells may be carried out by any method known in the art to be effective to selectively lyse cells with or without lysing microorganisms, including, without limitation, addition of a lysis solution, sonication, osmotic shock, chemical treatment, and/or a combination thereof.

The lysis solution is one that is capable of lysing cells, e.g., non-microorganism cells (e.g., by solubilizing or dissolving eukaryotic cell membranes) and/or microorganism cells. In one embodiment, the lysis solution can comprise one or more detergents, optionally one or more enzymes, or a combination of one or more detergents and one or more enzymes, and can further include additional agents. In one embodiment, the detergent can be a non-denaturing lytic detergent, such as TRITON® X-100, TRITON® X-100-R, TRITON® X-114, NP-40, GENAPOL® C-100, GENAPOL® X-100, IGEPAL® CA 630, ARLASOLVE™ 200, BRIJ® 96/97, CHAPS, octyl β-D-glucopyranoside, saponin, and nonaethylene glycol monododecyl ether (C12E9, polidocenol). Optionally, denaturing lytic detergents can be included, such as sodium dodecyl sulfate, N-laurylsarcosine, sodium deoxycholate, bile salts, hexadecyltrimethylammonium bromide, SB3-10, SB3-12, amidosulfobetaine-14, and C7BzO. Optionally, solubilizers can also be included, such as BRIJ® 98, BRIJ® 58, BRIJ® 35, TWEEN® 80, TWEEN® 20, PLURONIC® L64, PLURONIC® P84, non-detergent sulfobetaines (NDSB 201), amphipols (PMAL-C8), and methyl-β-cyclodextrin. Typically, non-denaturing detergents and solubilizers are used at concentrations above their critical micelle concentration (CMC), while denaturing detergents may be added at concentrations below their CMC. For example, non-denaturing lytic detergents can be used at a concentration of about 0.010% to about 10%, e.g., about 0.015% to about 1.0%, e.g., about 0.05% to about 0.5%, e.g., about 0.10% to about 0.30% (final concentration after dilution with the sample). In another embodiment, detergents comprising a hydrophilic polyoxyethylene "head" group linked to a hydrophobic alkane or alkene "tail" group by an ether bond may be preferred. These detergents are commonly specified using notation of the form $C_xE_y$, wherein "x" equals the number of carbons in the alkane or alkene chain, while "y" is the number of oxyethylene monomers ($CH_2CH_2O$) in the polyoxyethylene chain. Detergents of this type wherein x lies within the range of 10-20 and y lies within the range of 8-12 are preferred. Even more preferred are detergents of this type wherein x lies within the range of 12-18 and y lies within the range of 9-11. For example, the alkane-polyoxyethylene or alkene-polyoxyethylene detergent can be selected from the group consisting of BRIJ® 97, BRIJ® 96V, GENAPOL® C-100, GENAPOL® X-100 BRIJ® 97, BRIJ® 96V, GENAPOL® C-100, GENAPOL® X-100, nonaethylene glycol monododecyl ether (polidocanol), or a combination thereof.

Enzymes that can be used in lysis solutions include, without limitation, enzymes that digest nucleic acids and other membrane-fouling materials (e.g., proteinase, DNase, neuraminidase, polysaccharidase, GLUCANEX®, and PECTINEX®. Other additives that can be used include, without limitation, reducing agents such as 2-mercaptoethanol (2-Me) or dithiothreitol (DTT) and stabilizing agents such as magnesium, pyruvate, and humectants. The lysis solution can be buffered at any pH that is suitable to lyse the desired cells, and will depend on multiple factors, including without limitation, the type of sample, the cells to be lysed, and the detergent used. In some embodiments, the pH can be in a range from about 2 to about 13, e.g., about 6 to about 13, e.g., about 8 to about 13, e.g., about 10 to about 13. Suitable pH buffers include any buffer capable of maintaining a pH in the desired range, e.g., about 0.05 M to about 1.0 M CAPS. For some sample types (e.g., urine), the optimal pH for dissolution of unwanted cells and/or particulates may be from about 2 to about 8.

Further details and description of the lysis solutions contemplated in the practice of this invention are disclosed in co-pending U.S. patent application Ser. No. 12/589,929 (now published as US 2010/0129857 A1), filed Oct. 30, 2009, entitled "Methods for Isolation and Identification of Microorganisms," the contents of which are incorporated herein by reference.

The kit may also include at least one filter material (e.g., a filtration membrane) and/or device to isolate, accumulate and/or purify any microorganism that may be in test sample. In general, any filter material having pore sizes that retain at least some portions of the microorganisms and allow the lysate to pass through, can be used in the practice of this invention. The filter materials used in the practice of this invention may comprise, filter membranes or depth filters well known in the art. In one embodiment, the filter membrane will have a pore size of from about 0.1 µm to about 30.0 µm, or from about 0.1 µm to about 10.0 µm, or from about 0.1 µm to about 1.0 am. Exemplified membranes may include, polyethersulfone (PES) membranes (e.g., Express PLUS (Millipore, Billerica, Mass.) and SUPOR® 200, SUPOR® 450, SUPOR® MachV (Pall-Gelman, Port Washington, N.Y.)). Other possible filter materials may include, HT TUFFRYN® (polysulfone), GN METRICEL® (mixed cellulose ester), NYLAFLO® FP Verticel (PVDF), all from Pall-Gelman (Port Washington, N.Y.), and Nuclepore (polycarbonate) from Whatman (Kent, UK). Exemplified depth filter materials may include, type GF/F, GF/C and GMF150 (glass fiber, Whatman), GD/X combination filters (Whatman), spin filters (e.g., VectaSpin, Whatman), syringless filters (e.g., Mini-UniPrep, Whatman), METRIGARD® (glass fiber, Pall-Gelman), AP15 (glass fiber, Millipore), as well as a variety of cellulose, polyester, polyproplyene or other fiber or particulate filters, so long as the filter media can retain a sufficient number of the target microorganisms to enable analysis. In another embodiment, a charged or modified particulate or fiber filter material, for example, a zeta charged membrane, may be used. In yet another embodiment, the filtration process may be driven by centrifugation (e.g., VectaSpin filters from Whatman) or by positive pressure (e.g., Mini-UniPrep devices from Whatman).

In yet another embodiment, as previously discussed elsewhere herein, the may include one or more integrated filtration and sample transfer devices operable for separation, capture and accumulation of microorganisms from a test sample by vacuum filtration, and subsequent transfer of the captured and accumulated microorganisms (e.g., as a mass or film) to a test slide or plate for analysis or interrogation of the microorganisms (e.g., by mass spectrometry). In one embodiment, the filtration and sample transfer device comprises an integrated filtration and sample transfer device having a hollow elongated body (e.g., a cylindrical, hexagonal, or similarly shaped elongated hollow tube) having a first end or tip that is provided with, or capped with a filtration material (e.g., a filtration membrane) and a second end adapted for connection to a vacuum system or device. In a preferred embodiment, the filtration material (e.g., a filter membrane) is located adjacent to, and extending from, the first end or tip of the integrated filtration and sample transfer device. For example, the filtration material may be external from (i.e., extending or protruding from) the first end or tip of the elongated body. The present applicants have found that the use of a filtration material that extends from, or protrudes from, the first end of the integrated filtration and sample transfer device allows for the transfer of any isolated and/or accumulated microorganisms, e.g., by smearing or spotting of the sample on a plate or slide.

Figure 4B:
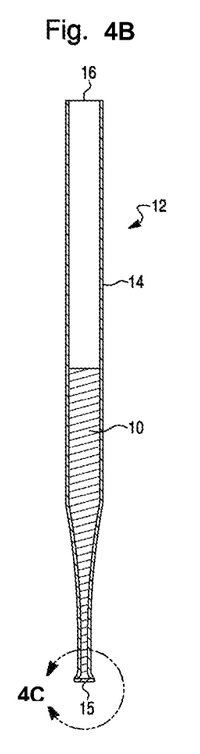
FIG. 4B shows a cross-sectional view of the device and FIG. 4C shows a detailed view of a first end of the device.
Figure 4C:
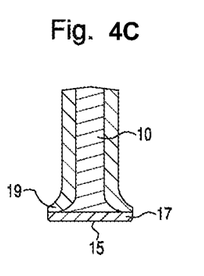
Figures 5A, 5B:
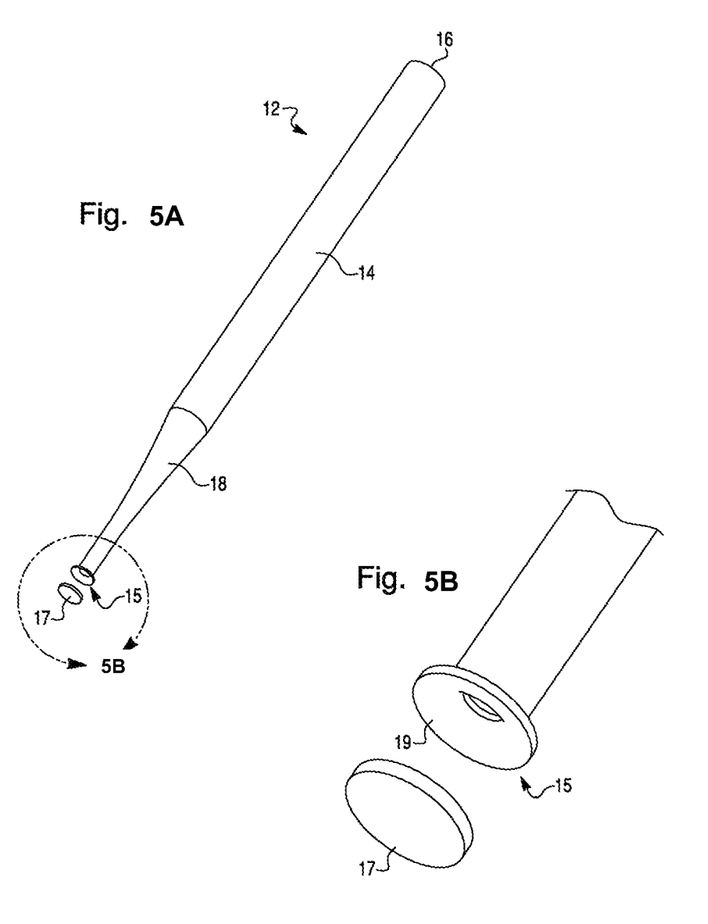
FIG. 5A shows an exploded view of the integrated filtration and sample transfer device illustrated in FIG. 3
FIG. 5B shows a detailed view of a first end of the device.

FIGS. 4-5 illustrates an integrated filtration and sample transfer device 12 comprising a hollow elongated cylindrical tube or body 14 having a first end 15 and a second end 16. The first end 15 is provided with, or capped with a filter material 17, which operates to capture or accumulate microorganisms when a vacuum or suction is applied to the integrated filtration and sample transfer device 12. In a preferred embodiment the filtration material 17 is adjacent to, and external from (i.e., extends from, or protrudes from), the first end or tip 15 of the elongated cylindrical tube or body 14. The first end 15 of the integrated filtration and sample transfer device 12 may further comprise a tapered portion 18 and a flared or flattened tip 19. In other embodiments, the second end 16 can be provided with a bulb or a plunger to provide a suction force for filtration. Also as shown, in one possible embodiment, the hollow cylindrical shaped body can be filled, or packed, with an adsorbent 10, as discussed hereinabove. In accordance with this embodiment, the adsorbent itself can provide a capillary action or wicking force that provides fluid flow for filtration.

In one embodiment, the hollow elongated body is made of glass. In another embodiment, the hollow elongated body is made of a rigid, or semi-rigid, plastic material, such as, polypropylene (PP), polycarbonate (PC), polyethylene terephthalate (PET), or other plastic material. In general, the integrated filtration and sample transfer device comprises an elongated generally cylindrical body having a filtration tip diameter of from about 0.5 mm to about 10 mm, from about 1 mm to about 5 mm, or from about 1.5 mm to about 3 mm. In another embodiment, the barrel of the cylinder can flare out to an even larger diameter to be able to contain an even larger volume of filtrate. The filtration and transfer device may have a length of from about 2 cm to about 20 cm, from about 3 cm to about 15 cm, or from about 4 cm to about 10 cm. In one embodiment, the integrated filtration and sample transfer device comprises an elongated cylindrical body having a diameter of about 1.5 mm to about 3 mm, and a length of about 4 cm to about 10 cm. In another embodiment, the integrated filtration and sample transfer device comprises an elongated cylindrical body having an internal volume of from about 0.5 $cm^3$ to about 10 $cm^3$, from about 1 $cm^3$ to about 5 $cm^3$, or from about 1.5 $cm^3$ to about 3.5 $cm^3$. In yet another embodiment, the integrated filtration and sample transfer device comprises an elongated cylindrical body having a diameter of about 1.5 mm to about 3 mm and a length of from about 4 cm to about 10 cm (or a volume from about 0.9 $cm^3$ to about 4.7 $cm^3$).

In one embodiment, the hollow elongated cylindrical tube of the integrated filtration and sample transfer device may be filled, or packed, with an adsorbent. Packing of an absorbent material behind the membrane is helpful in two ways. First, it provides support, which allowed the membrane to protrude slightly beyond the tip, which Applicants have found allows for a more efficient transfer of microorganisms from the filter material (e.g., a filter membrane) to a slide or target plate. Second, the use of an adsorbent in the filtration and transfer device also allows for the adsorption of the lysate (i.e., culture media and/or cell materials) that has passed through the filtration material. Moreover, Applicants have found that the packing material provides a clear separation zone between the sample lysate and filter membrane, thereby preventing remixing of the lysate filtrate back in contact with the membrane during and after washing, thus preventing recontamination of the clean microbes. In general, any known adsorbent material can be used. For example, in one embodiment, the adsorbent can be a polyester, glass or cellulose fiber or particulate material. In another embodiment, the adsorbent could be an adsorptive resin, a silica gel, a hydrogel, polyacrylic acid or polyacrylamide derivatives, vegetable gums, a molecular sieve, zeolite, or other adsorbents well known to those of skill in the art.

In accordance with the present invention, the first end or tip of the integrated filtration and sample transfer device is provided with, or capped with, a filter material (or filtration material). For example, as discussed elsewhere herein, the filtration material (e.g., a filter membrane) is located adjacent to, and extending from, the first end or tip of the integrated filtration and sample transfer device. In general, any filter material having pore sizes that retain at least some portions of the microorganisms and allow the lysate to pass through, can be used in the practice of this invention. The filter materials used in the practice of this invention may comprise, filter membranes or depth filters well known in the art. In one embodiment, the filter membrane will have a pore size of from about 0.1 µm to about 30.0 µm, or from about 0.1 µm to about 10.0 µm, or from about 0.1 µm to about 1.0 µm. Exemplified membranes may include, polyethersulfone (PES) membranes (e.g., SUPOR® 200, SUPOR® 450, SUPOR® MachV (Pall-Gelman, Port Washington, N.Y.), Millipore Express PLUS® (Millipore)). Other possible filter materials may include, HT TUFFRYN® (polysulfone), GN METRICEL® (mixed cellulose ester), NYLAFLO® (Nylon), FP Verticel (PVDF), all from Pall-Gelman (Port Washington, N.Y.), and Nuclepore (polycarbonate) from Whatman (Kent, UK). Exemplified depth filter materials may include, type GF/F, GF/C and GMF150 (glass fiber, Whatman), METRIGARD® (glass fiber, Pall-Gelman), AP15 (glass fiber, Millipore), as well as a variety of cellulose, polyester, polyproplyene or other fiber or particulate filters, so long as the filter media can retain a sufficient number of the target microorganisms to enable analysis. In another embodiment, a charged or modified particulate or fiber filter material, for example, a zeta charged membrane, may be used.

The kit will also include at least one wash buffer for washing the isolated, accumulated and/or purified microorganism or microorganism mass on the filter material. The wash buffer can be used to further separate, isolate or purify the accumulated or captured microorganisms by "washing" away other components (e.g., media, media components, cell-debris, non-microorganisms or components thereof) that may be present in the test sample. As one of skill in the art would readily appreciate, the use of a wash buffer allows, or facilitates, washing away (or pass through the filter material) media, media components, cell-debris, non-microorganisms or components thereof, which may otherwise interfere with subsequent testing (e.g., mass spectrometric analysis). The wash buffer may also be used to rapidly neutralize the alkaline pH of the lysis solution. In general, any known wash buffer can be included in the kit. For example, the wash buffer could be distilled water. In another embodiment, the wash buffer could be a pH buffer capable of maintaining a pH suitable for microorganisms, such as a phosphate, MOPS or TRIS buffer. For example, the wash buffer could be a 0.01 M to about 0.2 M phosphate solution, pH 6.0 to 7.5

Furthermore, the kit may also comprise a filtration device, vacuum source and/or a vacuum interface. The filtration device can be adapted for attachment to a vacuum source or vacuum system, which is operable for providing a vacuum for filtration (i.e, for vacuum filtration). In general, any known means in the art for connecting the filtration and sample transfer device to the vacuum system can be used. For example, the filtration and transfer device can be connected to a vacuum system with the use of a simple vacuum tube, as is well known in the art. For example, the kit may comprise a side-arm vacuum flasks (see FIGS. 2-3, number 30) with reusable filter holder or a manifold (see FIG. 3, number 32) with a filtrate reservoir and a plurality of reusable filter holders (see FIG. 3, number 34). In still other embodiments, the kit may further comprise additional components for filtration, for example, the kit may comprise one or more tubes, clamps, valves or vacuum traps. In another embodiment, the kit may comprise one or more disposable filtration devices having a built in filtration membrane. In these disposable devices, filtration may be driven by either a vacuum source of by centrifugation.

The kit may also include a container (e.g., a tube), within which the lysis step can be carried out. The container may be any container with sufficient volume to hold a test sample and optionally a lysis solution. In one embodiment, the container can be a tube. In another embodiment, the separation device disclosed in related U.S. patent application Ser. No. 12/589,969 (now published as US 2010/0120133 A1), filed Oct. 30, 2009, entitled "Separation Device for Use in the Separation, Characterization and/or Identification of Microorganisms", may be included in the kit. The volume of the container can be about 0.1 ml to about 25 ml, e.g., about 1 ml to about 10 ml, e.g., about 2 ml to about 8 ml. If the lysis step and subsequent isolation or separation step are done on a microscale, the volume of the container can be about 2 µl to about 100 µl, e.g., about 5 µl to about 50 µl. The container can have a closure device attached or may be threaded to accept a closure device (e.g., a cap) such that the container can be hermetically sealed during use. The presence of a closure decreases the risks from handling microorganisms that are or may be infectious and/or hazardous, as well as the risk of contaminating the sample.

In one embodiment, the kit may comprise, in packaged combination:

(a) a selective lysis solution comprising Brij 97 (Sigma) and CAPS (Alfa Aesar), for example, a 60 ml bottle of the selective lysis solution;

(b) at least one filtration membrane, for example a package comprising 50×0.45 µm filtration membranes (Millipore Express PLUS);

(c) a first wash buffer comprising Brij 97 detergent in a phosphate buffer ($Na_2PO_4$) containing NaCl, for example, a 200 ml bottle of wash buffer; and (d) a second wash buffer comprising DI Water, for example, a 200 ml bottle of DI Water.

Optionally, the kit may further comprise one or more of: at least one device for harvesting or collecting microorganisms from the filter material (or filter membrane) (e.g., a swab or scraper); at least one container (e.g., a tube) for carrying out the lysis step; and/or at least one transfer pipettes for transferring the sample or lysed sample to the filtration membrane and/or filtration device.

In general, the kit can be configured for processing any number of test samples (i.e., for the isolation, accumulation and/or purification of microorganisms from any specific number of test samples). For example, the kit can be configured for processing (isolating, accumulating and/or purifying microorganisms) from about 1 to about 1000 test samples, from about 10 to about 500 test samples, or from about 10 to about 100 test samples. In another embodiment, the kit could be configured for processing from about 10 to about 80 test samples, from about 20 to about 60 test samples, or about 50 test samples.

That which is claimed is:

1. A kit for the isolation, accumulation and/or purification of microorganisms from a test sample comprising, in a packaged combination:
   (a) a selective lysis buffer comprising Brij and CAPS for the selective lysis of non-microorganism known to be present or that may be present in a test sample;
   (b) a filtration device comprising a hollow elongated body having a first end and a second end, wherein the first end is capped with a 0.45 μm filtration membrane to prevent passage of microorganisms through the filtration membrane but allows other components in the test sample to pass through the filtration membrane, wherein the filtration membrane extends from the first end in a direction opposite the second end;
   (c) a wash buffer consisting of a Brij 97 detergent in a sodium phosphate buffer containing sodium chloride for washing the isolated, accumulated and/or purified microorganism sample;
   (d) a vacuum system configured to connect to the second end of the filtration device;
   (e) at least one micro-swab for harvesting or collecting microorganisms from the filtration membrane;
   (f) at least one disposable transfer pipette adapted to transfer the lysed sample to the filtration membrane; and
   (g) at least one MALDI-TOF target plate,
   wherein the swab is adapted for transferring the microorganisms from the filtration membrane to the MALDI-TOF target plate.

2. The kit of claim 1, wherein said lysis solution further comprises an enzymes composition comprising one or more proteinases and/or one or more nucleases.

3. The kit of claim 1, wherein said filtration membrane is selected from the group consisting of polyethersulfone (PES) membranes, polysulfone, mixed cellulose ester, polycarbonate, glass fiber type GF/F, GF/C and GMF150, GD/X combination filters, spin filters, syringless filters, cellulose, polyester, polyproplyene and other fiber or particulate filters.

4. The kit of claim 1, wherein said filtration device is disposable.

5. The kit of claim 1, wherein said kit further comprises one or more containers within which the lysis step can be carried out.

6. The kit of claim 1, wherein said kit is configured for processing from about 1 to about 500 test samples.

* * * * *